United States Patent [19]
Soehendra et al.

[11] Patent Number: 5,643,277
[45] Date of Patent: Jul. 1, 1997

[54] DEVICE FOR RETRIEVING STENTS

[75] Inventors: Nib Soehendra, Norderstedt; Carsten Grosse, Querkamp, both of Germany

[73] Assignee: Wilson-Cook Medical, Inc., Winston-Salem, N.C.

[21] Appl. No.: 284,349

[22] Filed: Aug. 2, 1994

Related U.S. Application Data

[60] Continuation of Ser. No. 19,984, Feb. 17, 1993, Pat. No. 5,334,208, which is a division of Ser. No. 549,601, Jul. 9, 1990, abandoned.

[51] Int. Cl.$^6$ .................................................. A61B 17/00
[52] U.S. Cl. ........................... 606/108; 600/104; 623/1; 623/12
[58] Field of Search ........................ 606/108, 198, 606/159, 191, 109; 128/898, 838, 840; 600/104; 623/1, 12

[56] References Cited

U.S. PATENT DOCUMENTS

| | | |
|---|---|---|
| 2,739,585 | 3/1956 | Ayre . |
| 4,665,918 | 5/1987 | Garza et al. .............. 606/108 |
| 4,699,611 | 10/1987 | Bowden . |
| 4,768,507 | 9/1988 | Fischell et al. ............ 606/108 |
| 5,047,040 | 9/1991 | Simpson et al. ............ 604/22 |
| 5,098,374 | 3/1992 | Othel-Jacobsen et al. .... 606/108 |

FOREIGN PATENT DOCUMENTS

| | | |
|---|---|---|
| 0364420 | 4/1990 | European Pat. Off. . |
| 0365269 | 4/1990 | European Pat. Off. . |
| 186005 | 9/1922 | France . |
| 3704094 | 8/1988 | Germany . |
| 8914061.3 | 4/1991 | Germany . |
| 674943 | 8/1990 | Switzerland . |
| 8800279 | 5/1988 | WIPO . |
| 8800146 | 9/1988 | WIPO . |

*Primary Examiner*—Michael H. Thaler
*Attorney, Agent, or Firm*—Woodard, Emhardt, Naughton, Moriarty & McNett

[57] ABSTRACT

A technique for removing an implanted stent and a device useful therefor. An endoscope is introduced into position at the proximal end of the implanted stent and a cannula is then introduced through the endoscope. A wire guide is then passed through the cannula and into the duct through the lumen of the stent which is to be removed. The cannula is then removed and a stent retrieval cable is advanced over the wire guide and into position at the proximal end of the stent. The stent retrieval cable is torqueable, and has a tapered thread at its distal end and a rotation dial at its proximal end. Once the retrieval cable has been placed into position, the rotation dial is turned to engage the threading into the lumen of the stent. After the stent has been attached to the retrieval cable in this manner, the stent and cable are removed together through the endoscope and out of the body, leaving the endoscope and wire guide in place for use in the implantation of the replacement stent.

7 Claims, 8 Drawing Sheets

DEVICE FOR RETRIEVING STENTS

This application is a continuation of application Ser. No. 08/019,984, filed Feb. 17, 1993, issuing into U.S. Pat. No. 5,334,208 on Aug. 2, 1994, which is a divisional of Ser. No. 07/549,601, filed on Jul. 9, 1990, now abandoned.

BACKGROUND OF THE INVENTION

It is common medical practice today to implant stents within the body to maintain openings within certain passages therein. For instance, a biliary stent might be implanted to ensure drainage through an obstructed bile duct. Stents are configured in a variety of shapes and sizes, depending upon the location and purpose of the intended implantation, and the personal preference of the attending physician.

When a stent needs to be replaced or removed, prior to the present invention, the procedure for removal has been standardly performed with the use of retrieval forceps, baskets, or snares. Such devices are used to grasp the proximal end of the implanted stent. After the stent has been firmly grasped, it is pulled through the duct and out of the body.

There are several attendant disadvantages with this heretofore commonly used practice for removing implanted stents from within the body. For one thing, the actual process of technically grasping and pulling the stent out of its implanted position evenly and atraumatically can sometimes be difficult to perform, particularly for the larger sized stents. Where the stent has not been and pulled out evenly, bleeding and/or scaring can result, which can cause trauma and possible aggravation of the problem of occlusion that is being treated. Yet another significant complication concerns the fact that, when grasped by a retrieving device, the stent will most often not fit within the channel of the endoscope. The endoscope must therefore be removed in order to allow for the retrieval of the stent, and then be repositioned again for the replacement procedure. The requirement of recannulation adds considerable time to the overall replacement process.

Implanted stents need to be regularly removed and replaced since they, themselves, tend to become occluded after a period of time. Owing at least partially to the relative difficulty involved in replacement, much has been done in the way of attempting to extend the useful life of an implanted stent. What is needed is an improved method and apparatus for removing stents that have been implanted within the body, which would facilitate replacement in an atraumatic way.

SUMMARY OF THE INVENTION

Generally speaking, the present invention relates to a new and improved method for removing an implanted stent from within the body, and to a new device which is useful to accomplish this result. According to one embodiment of the method of the present invention where a biliary stent is to be removed from the common bile duct, an endoscope is first introduced into position at the papilla of vater. Then, a cannula is introduced through the endoscope and a wire guide is then passed through the cannula and into the bile duct through the lumen of the biliary stent which is to be removed. The cannula is then removed and a stent retrieval cable is advanced over the wire guide and into position at the proximal end of the stent. The stent retrieval cable is torqueable, and has a threaded portion at its distal end and a rotation dial at its proximal end. Once the retrieval cable has been placed into position, the rotation dial is turned to engage the threading into the lumen of the stent. After the stent has been attached to the retrieval cable in this manner, the stent and cable are removed together through the endoscope and out of the body, leaving both the endoscope and wire guide in place for use in the implantation of the replacement stent.

BRIEF DESCRIPTION OF THE DRAWINGS

FIGS. 1a through 1d illustrate a sequence of steps in the removal of an implanted stent from the common bile duct of a patient.

In FIG. 1a, an endoscope has been positioned at the papilla of vater, and a cannula has been advanced through the channel of the endoscope and into axial alignment with the implanted stent.

FIGS. 2a through 2c are enlarged views of the area about the proximal end of the stent and the distal end of the endoscope for FIGS. 1a through 1c respectively.

FIGS. 3a through 3c are side elevational views of the components used in the described procedure for removing an implanted biliary stent.

FIG. 3b is an illustration of wire guide 80.

FIG. 3c is an illustration of introduction cannula 70.

FIGS. 4a through 4c are enlarged, segmented, cross sectional views of various portions of stent retrieval cable 90 in combination with wire guide 80 and stent 10.

FIG. 4a is a segmented cross sectional view of the proximal end portion of stent retrieval cable 90, as seen along line 4a—4a of FIG. 3a, and with wire guide 80 positioned within the interior passageway thereof.

FIG. 4b is a cross sectional view of the shaft of stent retrieval cable 90, as seen along line 4b—4b of FIG. 3a.

FIG. 4c is a segmented cross sectional view of stent retrieval cable 90, as seen along line 4c—4c of FIG. 3a, with wire guide 80 positioned within the interior passageway thereof, and where stent retrieval cable 90 has been threadedly engaged with the lumen of stent 10.

DESCRIPTION OF THE PREFERRED EMBODIMENT

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Referring now to the drawings, FIGS. 1a through 1d illustrate the sequencing of steps whereby an implanted biliary stent 10 is removed from the common bile duct 20. Biliary stent 10 is made of radiopaque polyethylene. Stent 10 includes a distal end 11, and distal drainage holes 12, as well as a proximal flap 13 near the proximal end 15 of stent 10, and proximal drainage holes 14. The placement of biliary stent 10 facilitates the drainage of bile fluids from hepatic ducts 30, through common bile duct 20, and out through the papilla of vater 40 towards the small intestines 50. It is to be appreciated that the biliary stent, as shown and described, is illustrative in nature as a suitable stent for use with the present invention, and that other stents of differing configurations, compositions, and locations of implantation, are contemplated to be suitable for use with the present invention as well.

Figure 1A:
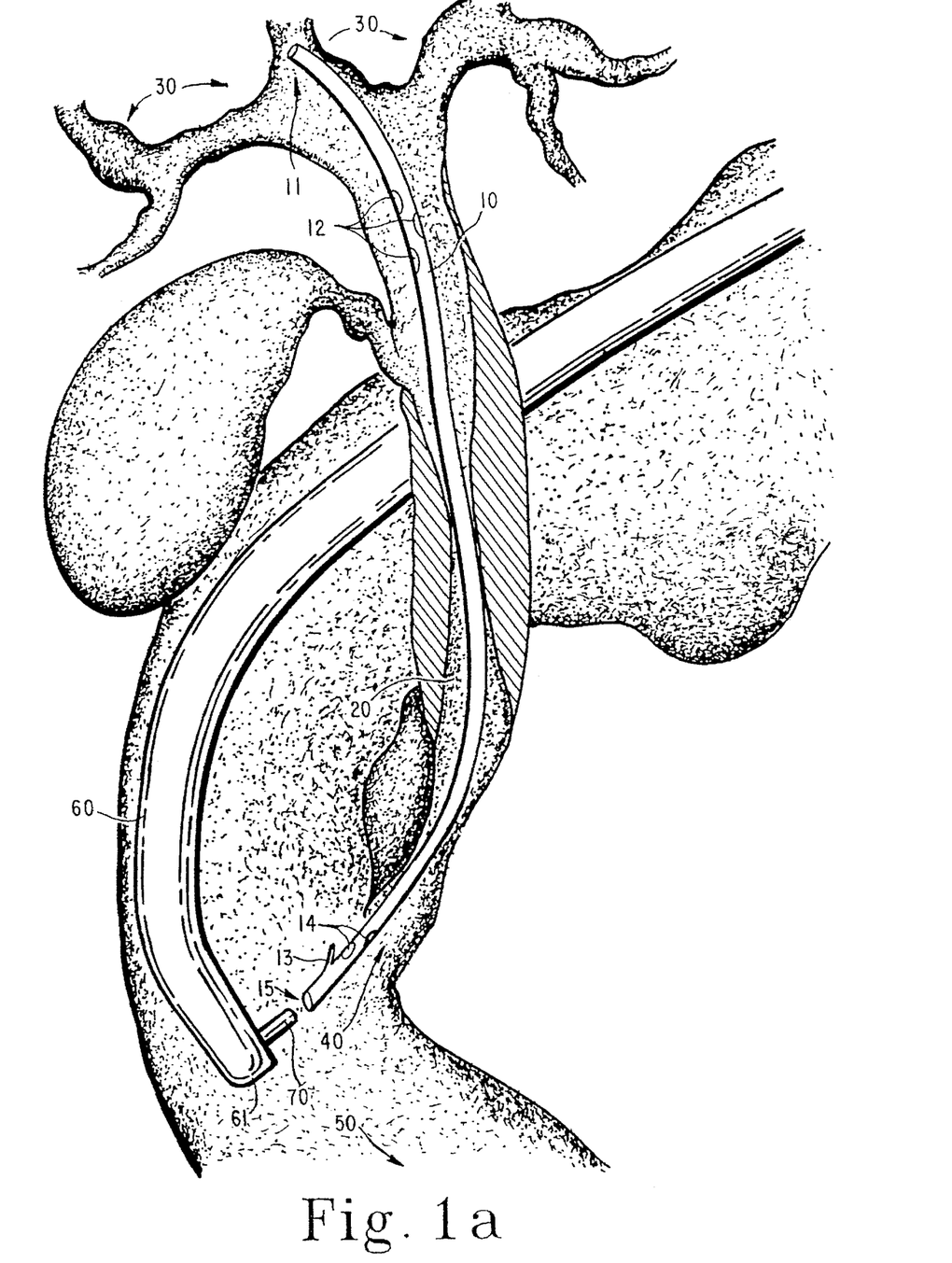
FIG. 1a is a side view of a biliary stent implanted in the common bile duct of a patient.

To begin the procedure for removal of stent 10, an endoscope 60 is first introduced into position at the papilla of vater 40. Then, a cannula 70 is introduced through the channel of endoscope 60 and into position in axial alignment with the proximal end 15 of stent 10. FIG. 1a illustrates the stage of the procedure where endoscope 60 and cannula 70 have been so placed.

Figure 1B:
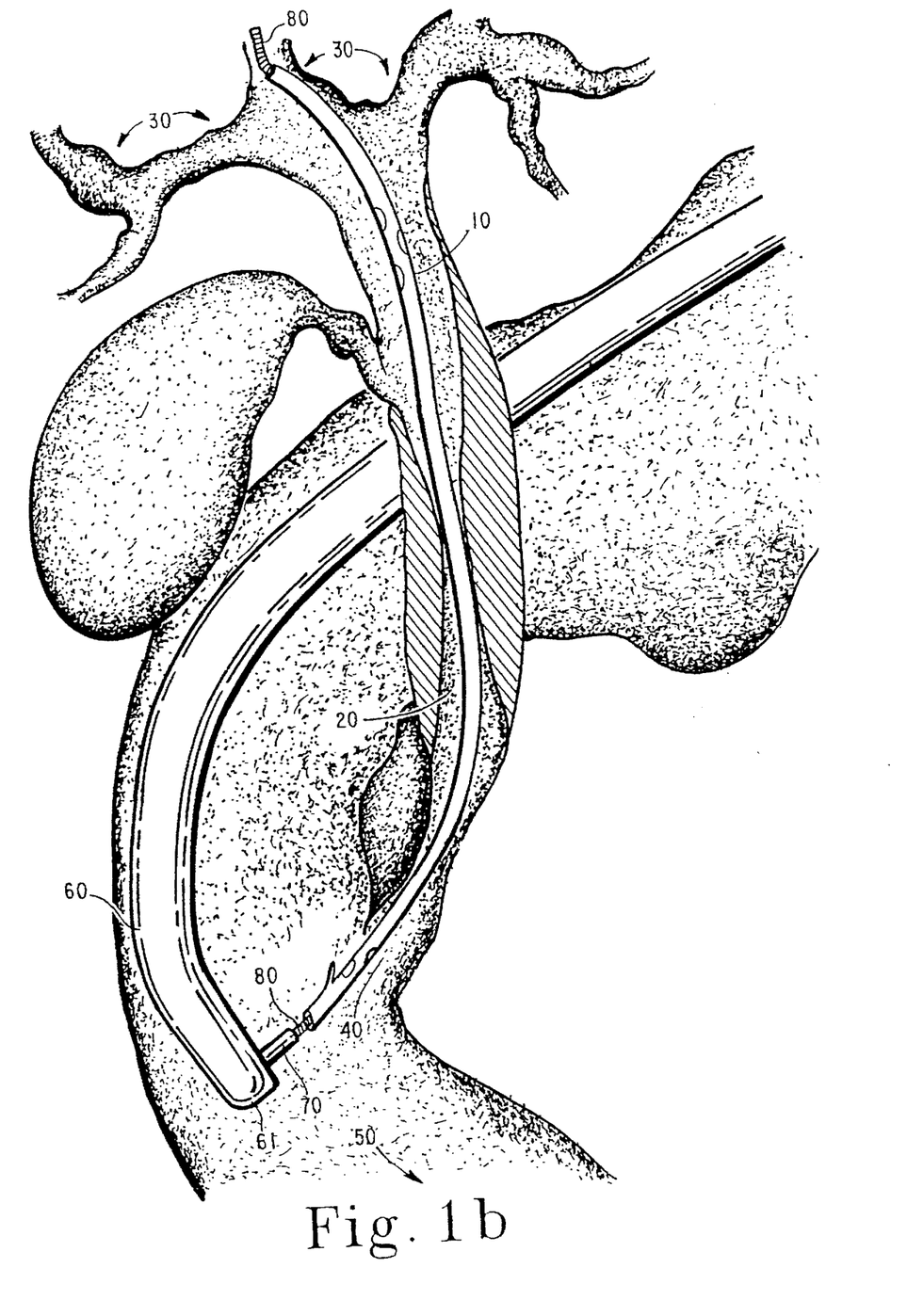
In FIG. 1b, a wire guide has been passed through the cannula and through the lumen of the implanted stent.
Figure 1C:
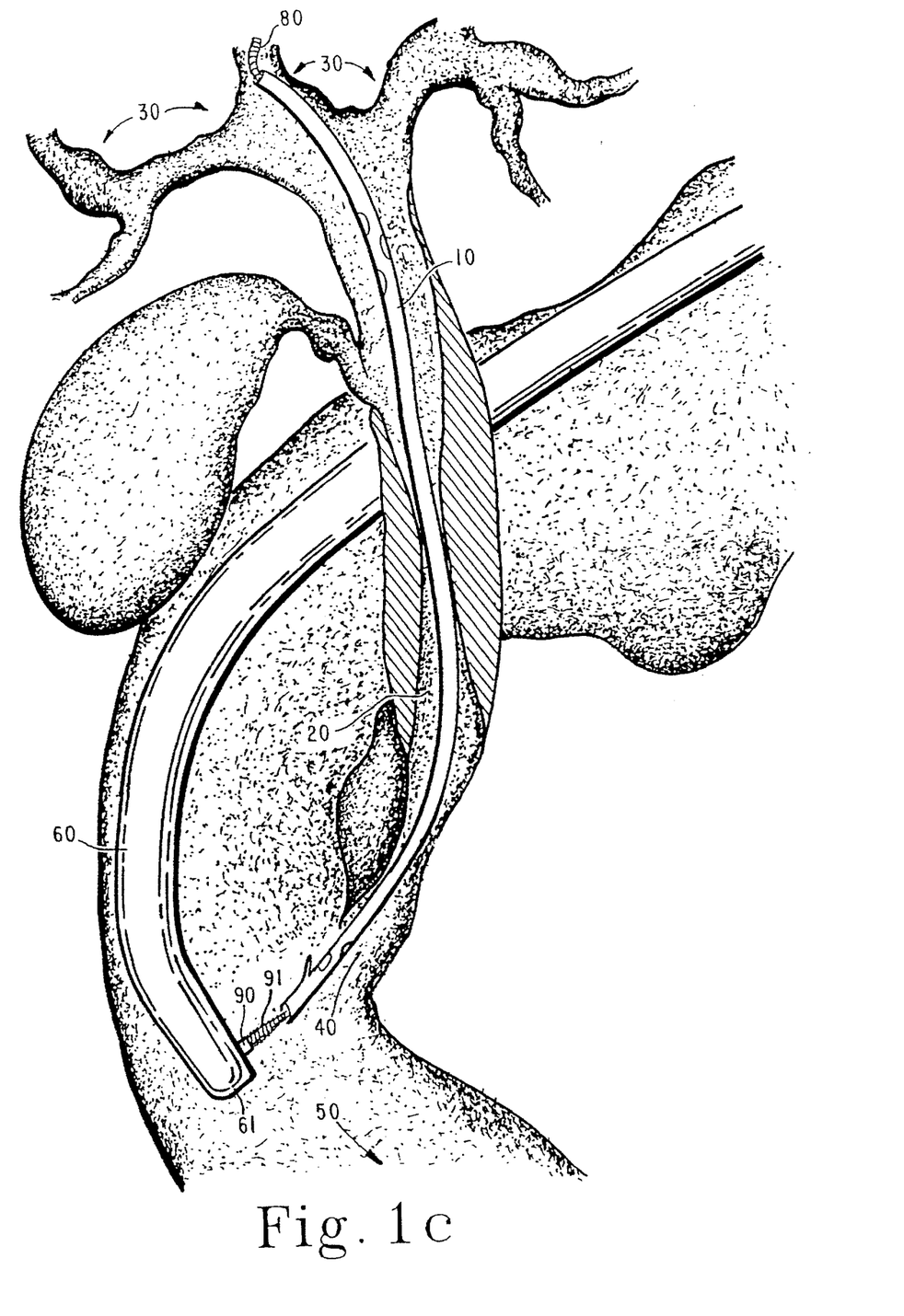
In FIG. 1c, the cannula has been removed, and a stent retrieval cable has been advanced along the wire guide and into position for threaded engagement with the stent.

As shown in FIG. 1b, a wire guide 80 is then passed through cannula 70 and into bile duct 20 through the lumen of stent 10. Cannula 70 is then removed and a stent retrieval cable 90 is advanced over wire guide 80 and into position at the proximal end 15 of stent 10. Stent retrieval cable 90 is torqueable, and has a threaded portion 91 at its distal end and a rotation dial 92 at its proximal end (see FIG. 3a). FIG. 1c illustrates the stage of the procedure where cannula 70 has been removed and stent retrieval cable 90 has been advanced along wire guide 50 and into position for threaded engagement with stent 10.

Figure 1D:
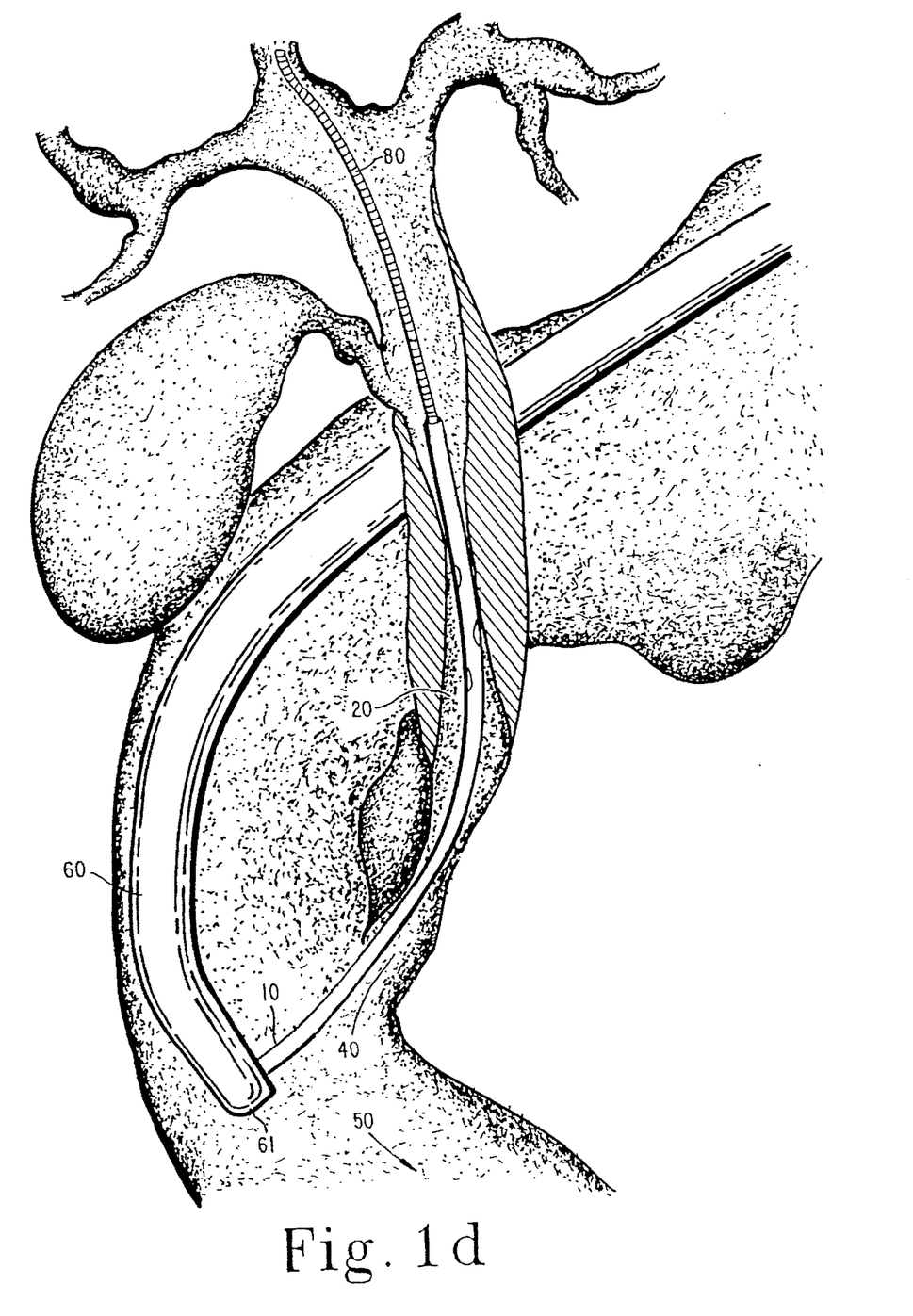
FIG. 1d illustrates the stent, which has been threadedly attached to the retrieval cable, being pulled through the channel of the endoscope and out of the body of the patient.

Once retrieval cable 90 has been placed into position, rotation dial 92 is turned to engage threading 91 into the lumen of stent 10. After stent 10 has been attached to retrieval cable 90 in this manner, stent 10 and cable 90 are removed together through the channel of endoscope 60 and out of the body of the patient, leaving both endoscope 60 and wire guide 80 in place for use in the implantation of the replacement stent. FIG. 1d illustrates this point of the procedure where stent 10, which has been threadedly attached to retrieval cable 90, is being pulled through the channel of endoscope 60 and out of the body of the patient.

Figure 2A:
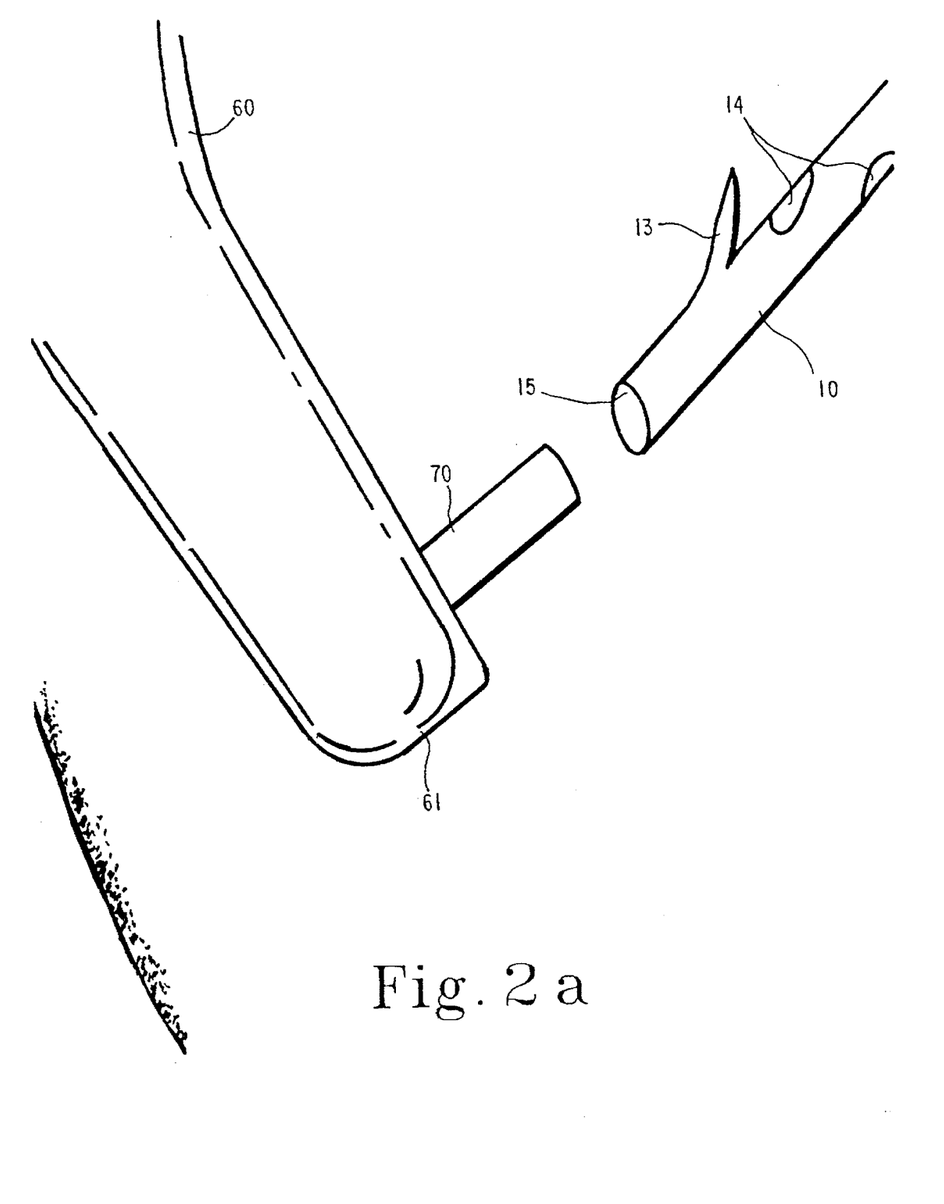
FIG. 2a illustrates the axial alignment of the introduction cannula with the proximal end of the implanted stent.
Figure 2B:
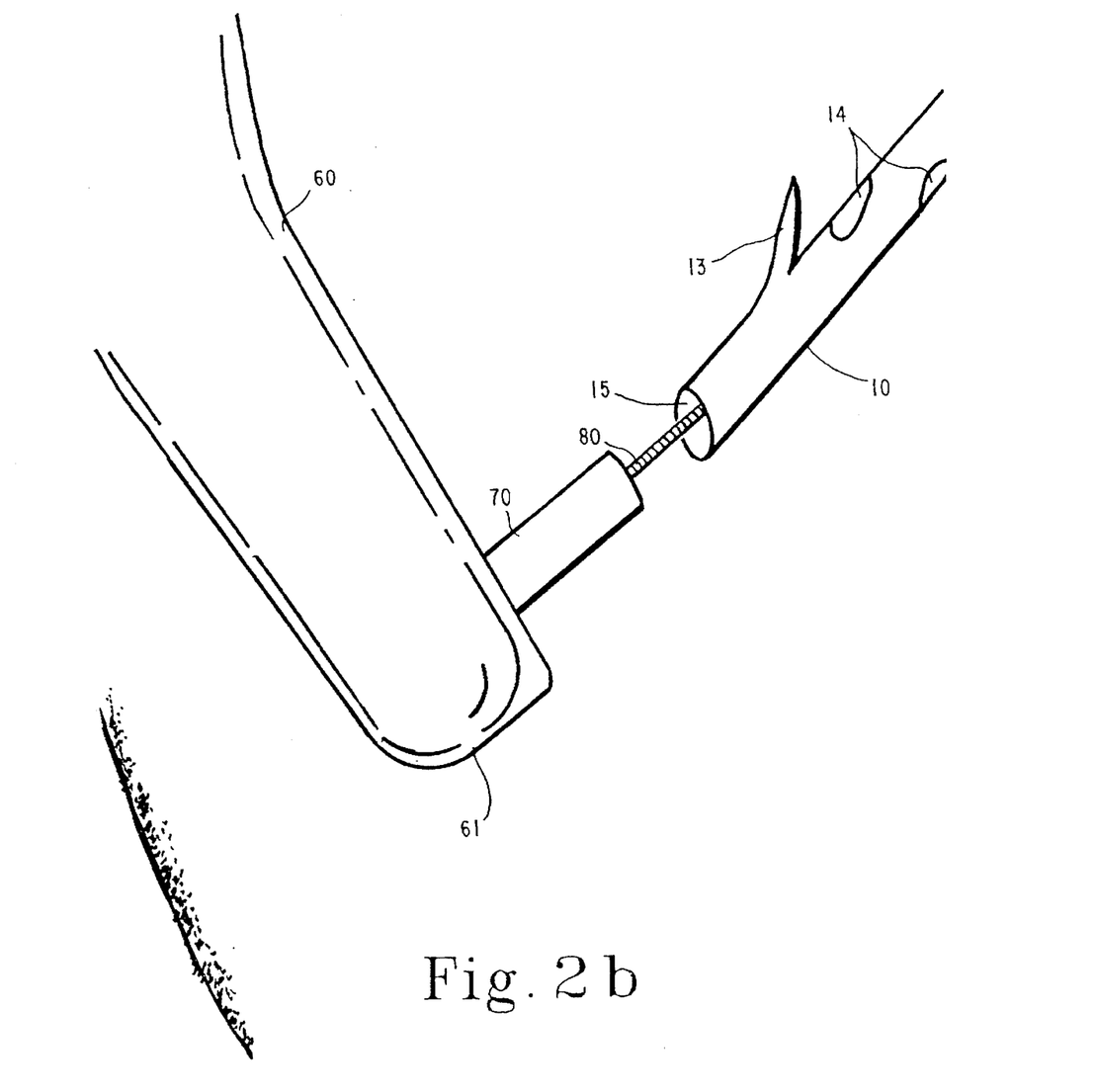
FIG. 2b shows the wire guide having been advanced through the cannula and into the lumen of the stent.
Figure 2C:
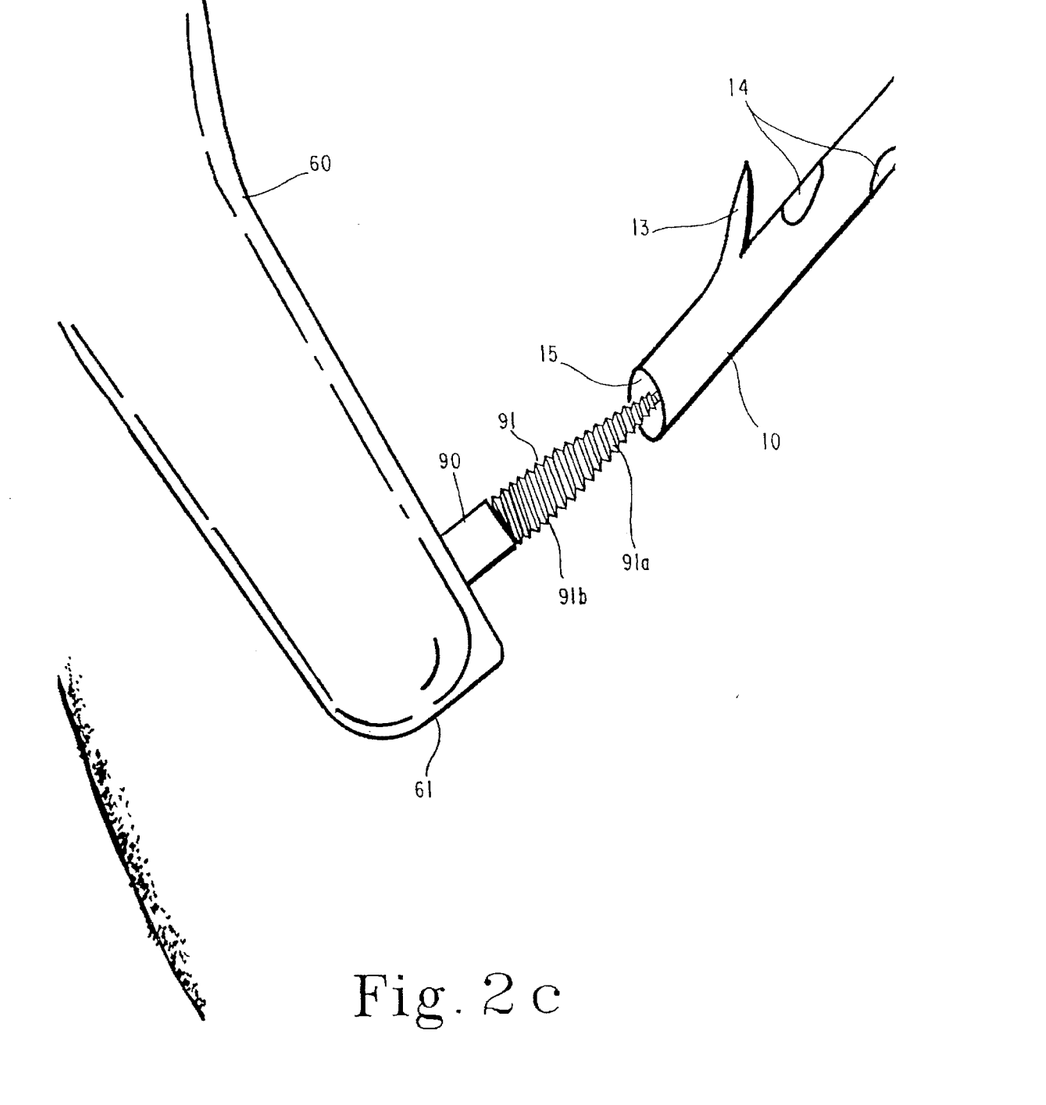
FIG. 2c is a detailed view of the retrieval cable in position for threaded engagement with the lumen of the stent to be removed.

FIGS. 2a through 2c are enlarged views of the area about the proximal end 15 of stent 10 and the distal end 61 of endoscope 60 at the points of the procedure above described and illustrated by FIGS. 1a through 1c respectively. From the detailed view of FIG. 2c, it can be seen that the threaded portion 91 of retrieval cable 90 includes a first tapered portion 91a, and a second cylindrical threaded portion 91b. First tapered threaded portion 91a allows for ease of initial engagement into the relatively soft lumen of stent 10, while second cylindrical threaded portion 91b provides reliable anchoring of cable 90 into the lumen of stent 10 through the continued threading of portion 91b into lumen of stent 10.

Figure 3A:
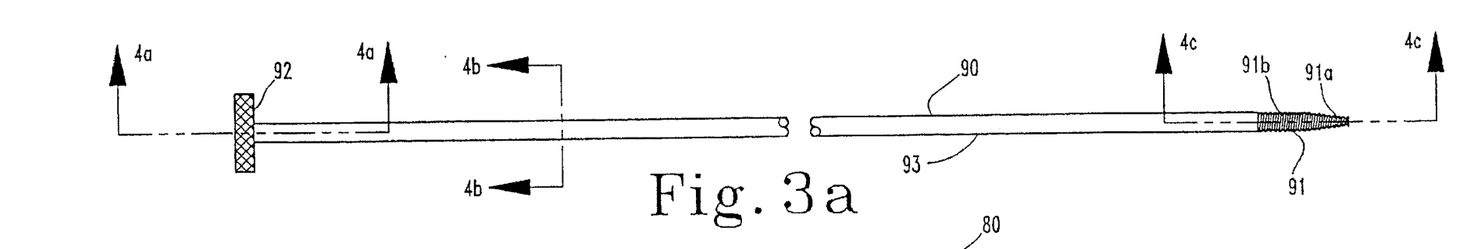
FIG. 3a is an illustration of stent retrieval cable 90.
Figures 3B, 3C, 4A, 4B, 4C:
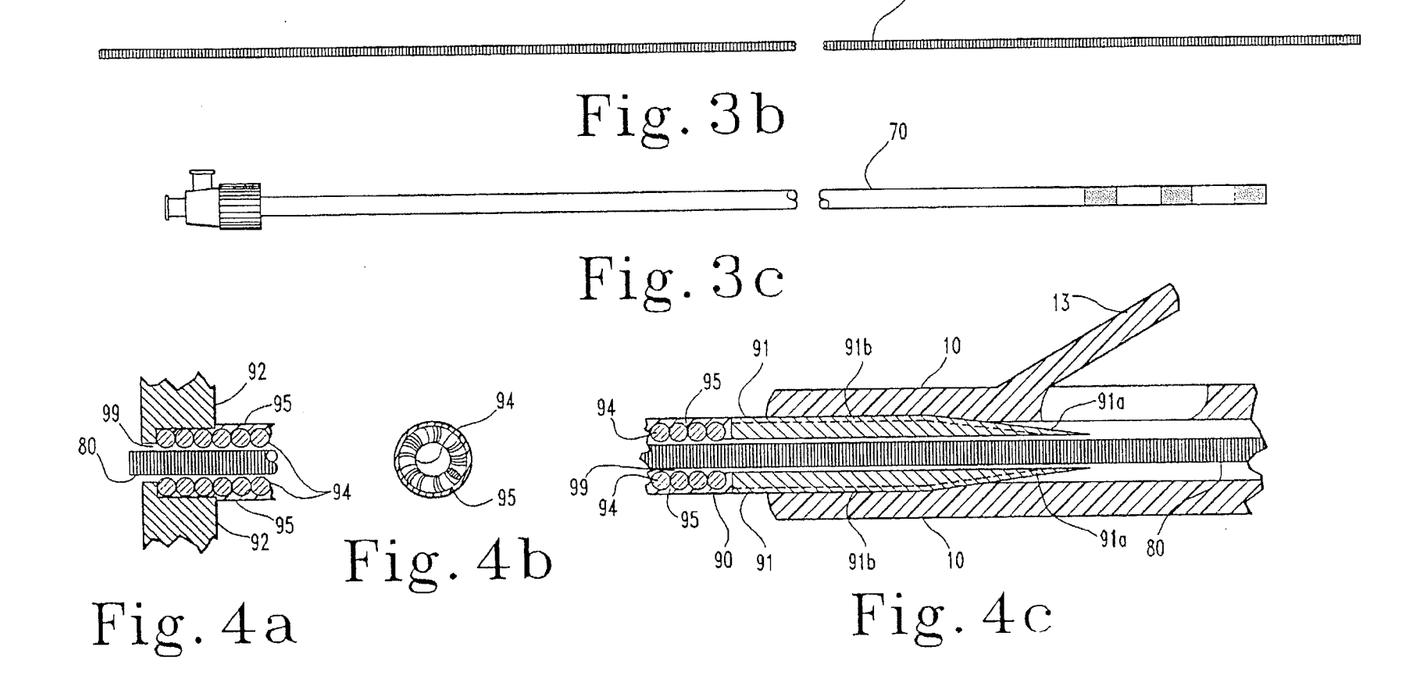

FIGS. 3a through 3c are side elevational views of the components used in the above described procedure for removing an implanted biliary stent from the common bile duct. FIG. 3a is an illustration of stent retrieval cable 90, and shows, at the distal end of cable 90, threaded portion 91, which includes a first far distal tapered threaded portion 91a, and a second cylindrical threaded portion 91b proximal thereto. As shown by FIG. 3a, cable 90 further includes rotation dial 92 at its proximal end, and torqueable shaft 93 along the length thereof.

FIG. 3b is an illustration of wire guide 80, which is of conventional construction suitable for introduction through the interior passageway of introduction cannula 70, and for guidance of stent 10 and stent retrieval cable 90 through the placement thereof within their respective interior passageways. FIG. 3c is an illustration of introduction cannula 70 which is also of conventional construction.

FIGS. 4a through 4c are enlarged, segmented, cross sectional views of various portions of stent retrieval cable 90 in combination with wire guide 80 and stent 10. FIG. 4a is a segmented cross sectional view of the proximal end portion of stent retrieval cable 90, as seen along line 4a—4a of FIG. 3a, and with wire guide 80 positioned within the interior passageway 99 thereof. As shown in FIG. 4a, torqueable shaft 93 is constructed of spiraled stainless steel wiring 94, about which has been applied a coating of Teflon material 95. Wiring 94 defines an interior passageway 99 therewithin through which is receivable wire guide 80. Rotation dial 92 is soldered to wiring 94 at the proximal end of shaft 93 and serves to facilitate the torqueing of cable 90 whereby cable 90 may be threadably engaged with stent 10.

FIG. 4b is a cross sectional view of the shaft of stent retrieval cable 90, as seen along line 4b—4b of FIG. 3a. FIG. 4b shows the spiraling of wire 94 which provides for the torqueability of cable 90, and serves to transfer the rotation of rotation dial 92 at the proximal end of the cable 90 into the rotation of threaded portion 91 at the distal end of cable 90. FIG. 4b also provides a good view of Teflon coating 95 about the circumference of wiring 94. By providing a smooth outer surface, Teflon coating 95 serves to facilitate insertion and removal of cable 90.

FIG. 4c is a segmented cross sectional view of stent retrieval cable 90, as seen along line 4c—4c of FIG. 3a, with wire guide 80 positioned within the interior passageway 99 thereof, and where stent retrieval cable 90 has been threadedly engaged with the lumen of stent 10. Threaded portion 91 is soldered to wiring 94 at the distal end of shaft 93 and serves to form the attachment with stent 10 whereby stent 10 may be removed from the body through the channel of endoscope 60. As previously mentioned, threaded portion 91 includes at far distal tapered threaded portion 91a which facilitates the initiation of threaded engagement into the lumen of stent 10, and also includes a second cylindrical threaded portion 91b which is proximal thereto. By the continued threading of threaded portion 91 into the lumen of stent 10, the threaded engagement of cylindrical threaded portion 91b into stent 10 serves to firmly anchor cable 90 into stent 10 whereby stent 10 may be reliably removed.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. In combination, a stent and instrumentation for retrieving the stent from within a patient's body, comprising:
    a stent adapted to be implanted within the patient's body, said stent having a proximal end opposite a distal end, and defining a lumen therethrough, said stent including an inner wall surrounding said lumen;

an endoscope, said endoscope having a proximal end and a distal end, said endoscope being configured for positioning with said proximal end outside of the patient's body and said distal end within the patient's body proximal to the proximal end of said stent, said endoscope defining a channel therethrough; and a retrieval cable, said retrieval cable being advanced through the channel of said endoscope, said cable including a proximal end configured for positioning outside the patient's body, and a distal end configured for positioning within the patient's body, the distal end having a threaded portion with a closed outer surface defining at least one of a generally cylindrical body portion and a tapered body portion, said threaded portion including a helical thread projecting from said at least one of said generally cylindrical body portion and said tapered body portion to form a ridge along said outer surface, at least a portion of said threaded portion being positioned within said lumen and said thread being attachedly engaged to said inner wall to thereby form an attachment between said retrieval cable and said stent and wherein the attached combination of said retrieval cable and said stent are removable through the channel of said endoscope and out of the body.

2. The combination of claim 1, further comprising a cannula, said cannula being introducable through the channel of said endoscope and into axial alignment with the proximal end of said stent.

3. The combination of claim 2, further comprising a wire guide, said wire guide being introducable through said cannula and into the interior of the lumen of said stent; and wherein said retrieval cable defines a passageway therethrough through which said stent retrieval cable is advanced over said wire guide through said endoscope and into alligned contact with the proximal end of said stent to thereby facilitate the attached engagement of the threaded portion of said retrieval cable to the lumen of said stent.

4. The combination of claim 1, further comprising a wire guide, said wire guide being introducable through the channel of said endoscope and into the interior of the lumen of said stent; and wherein said retrieval cable defines a passageway therethrough through which said stent retrieval cable is advanced over said wire guide through said endoscope and into alligned contact with the proximal end of said stent to thereby facilitate the attached engagement of the threaded portion of said retrieval cable to the lumen of said stent.

5. The combination of claim 1, wherein said threaded portion has both said generally cylindrical body portion and said tapered body portion, and said generally cylindrical body portion is integrally attached to said tapered body portion and positioned proximal thereto.

6. In combination, a stent and instrumentation for retrieving the stent from within a patient's body, comprising:

a stent adapted to be implanted within the patient's body, said stent having a proximal end opposite a distal end, and said stent defining a lumen therethrough, said lumen being adjacent an inner wall;

an endoscope, said endoscope having a proximal end and a distal end, said endoscope being configured for positioning with said proximal end outside of the patient's body and said distal end within the patient's body proximal to the proximal end of said stent, said endoscope defining a channel therethrough;

a retrieval cable, said retrieval cable being advanced through the channel of said endoscope, said cable including a proximal end configured for positioning outside the patient's body, and a distal end configured for positioning within the patient's body, said cable having a shaft and a threaded portion attached to said shaft at said distal end, a minimum diameter of said shaft being at least equal to a maximum diameter of said threaded portion, said threaded portion having a closed outer surface defining a generally cylindrical portion and a tapered portion distal to said cylindrical portion, said threaded portion further having a helical thread projecting from said cylindrical and tapered portions, and at least a portion of said threaded portion being anchored within said lumen by embedding said thread into said inner wall to thereby form an attachment between said retrieval cable and said stent for removal of the attached combination of said retrieval cable and said stent through said channel of said endoscope and out of the patient's body; and wherein said cable defines an inner passageway configured to receive a wire guide therethrough, said threaded portion has an inner surface opposite said outer surface, said inner surface surrounds said inner passageway, and said threaded portion has a cross-section with a solid annular shape between said inner and outer surfaces.

7. The combination of claim 6, further comprising a cannula, said cannula being introducable through the channel of said endoscope and into axial alignment with the proximal end of said stent.

* * * * *